United States Patent
Driemel

(10) Patent No.: US 8,190,237 B2
(45) Date of Patent: May 29, 2012

(54) MRI ADJUSTABLE HEAD COIL

(75) Inventor: Daniel Driemel, Oederan (DE)

(73) Assignee: Siemens Aktiengesellschaft, Munich (DE)

( * ) Notice: Subject to any disclaimer, the term of this patent is extended or adjusted under 35 U.S.C. 154(b) by 1358 days.

(21) Appl. No.: 11/760,874

(22) Filed: Jun. 11, 2007

(65) Prior Publication Data

US 2008/0007259 A1   Jan. 10, 2008

(30) Foreign Application Priority Data

Jun. 12, 2006   (DE) .......................... 10 2006 027 189

(51) Int. Cl.
*A61B 5/05* (2006.01)

(52) U.S. Cl. ........................................ 600/422; 600/407

(58) Field of Classification Search .................. 600/407, 600/410, 411, 415, 421, 422
See application file for complete search history.

(56) References Cited

U.S. PATENT DOCUMENTS

| | | | |
|---|---|---|---|
| 4,539,715 A * | 9/1985 | Clement | 2/420 |
| 4,587,493 A * | 5/1986 | Sepponen | 324/319 |
| 5,515,546 A * | 5/1996 | Shifrin | 2/410 |
| 5,552,707 A | 9/1996 | Takahashi et al. | |
| 7,526,330 B1 * | 4/2009 | Randell et al. | 600/421 |
| 2006/0293867 A1 * | 12/2006 | Wallner | 702/139 |
| 2008/0005841 A1 * | 1/2008 | Zelnik et al. | 5/601 |

FOREIGN PATENT DOCUMENTS

| | | |
|---|---|---|
| DE | 44 30 646 A1 | 3/1995 |
| DE | 100 52 192 C2 | 10/2002 |
| WO | WO2008073512 * | 6/2008 |

OTHER PUBLICATIONS

"Kopfspule für die MR-Bildgebung mit optimierter Sichtfreiheit," Thomas et al., Siemens Technik Report, vol. 2, No. 5 (Oct. 1999).

"Kombination aus Kopffixation and Kopfspule für neurochirurgische Operationen," Nimsky et al., Siemens Technik Report, vol. 3, No. 6 (Jan. 2000).

* cited by examiner

*Primary Examiner* — Tse Chen
*Assistant Examiner* — Rochelle Reardon
(74) *Attorney, Agent, or Firm* — Schiff Hardin LLP

(57) ABSTRACT

A head coil arrangement for a magnetic resonance device has a housing on or in which a number of coils are arranged, the housing having at least two housing parts that can be moved toward each other for adjustment to different head sizes.

20 Claims, 6 Drawing Sheets

MRI ADJUSTABLE HEAD COIL

BACKGROUND OF THE INVENTION

1. Field of the Invention

The present invention relates to a head coil arrangement for a magnetic resonance device, of the type having a housing on or in which a number of coils are arranged.

2. Description of the Prior Art

Head coil arrangements of the above type are known and are used in magnetic resonance devices as radio-frequency transmitting and receiving coils. If the coils operate in a receiving mode, the size of the coils in relation to the size of the test object plays a decisive role in the resulting signal-to-noise ratio. The signal-to-noise ratio is optimal if the coils rest as close as possible to the surface of the examination object, in this case the head.

In the prior art various head coil arrangements are known that are constructed so as to be suitable for at least 95% of all head sizes. By taking account of patient comfort and noise-protection, in particular by allowing space for headphones, a relatively large internal diameter results for the head coil arrangement. This is particularly the case when heads in a stereotaxic frame are to be enclosed by the coils. The head coil arrangement is therefore disadvantageously too large for some of the heads that are to be examined, resulting in a large spacing of the individual coils from the test object, i.e. the head, and therefore a poor signal-to-noise ratio.

In particular when developing new head coil arrangements with a relatively large number of individual coils the known construction is problematical due to the multiplication of the receiving channels, since the required individual coils become smaller and an improved signal-to-noise ratio is therefore indispensable in order to attain sufficiently good signal quality.

SUMMARY OF THE INVENTION

An object of the present invention is to provide a head coil arrangement that is suitable for a large number of head sizes and still has an improved signal-to-noise ratio.

This object is achieved in accordance with the invention by a head coil arrangement of the type described above wherein the housing has at least two housing parts that can be moved toward each other for adjustment to different head sizes.

According to the invention the housing of the head coil arrangement is divided along at least one line. In the simplest case two halves of the housing formed on one side as an open hollow body from the housing parts, the two halves being moveable toward each other. As a result, the volume inside the housing, in which a head may be received, is reduced; the coils may consequently be brought closer to the examination object, the head. In a particularly advantageous manner the at least two housing parts may be continuously moved toward each other. The head coil arrangement may then be individually adjusted to the head being examined, so the spacing of the individual coils from the head is also optimized.

The optimal adjustment to the respective head size achieves an improved signal-to-noise ratio since the proximity to the head allows higher signal intensity. This is particularly advantageous in the case of functional imaging since very low signal intensities are used in this sector. Signal losses are thus minimized by the head coil arrangement according to the invention.

The mobility of the parts can be achieved various ways according to the invention. Thus the housing parts may be linearly moved toward each other. Due to the conditions of symmetry a linear movement of this kind, in particular in the lengthwise and/or transverse direction(s) of a head that is to be received, is expedient. The housing parts can in the process each be guided with the aid of a linear guide.

In an alternative embodiment the housing parts can be swiveled toward each other. A hinge, for example, may be provided in this case, so the head coil arrangement may be opened for a larger internal volume and may be closed further for a smaller internal volume.

In a particularly advantageous embodiment, in the case of four housing parts each covering substantially one quarter of a head, each housing part can be linearly moved in two perpendicular directions, in particular in the lengthwise and transverse directions of the head, with respect to one adjacent housing part, respectively. The housing is divided into four quarters in this embodiment and each housing part can be linearly moved in two directions. This mobility is expedient along the imaginary dividing axes of a complete housing, which axes run in particular in the lengthwise and transverse directions of the head. Ultimately this makes even more precise adjustment possible than with just two housing parts, namely an adjustment in two directions that are perpendicular to each other. Asymmetrical examination object shapes, especially head shapes, may be better taken into account. In this embodiment the housing parts can each be guided by two linear guides. One linear guide for example may be guided in the other in this embodiment.

When the housing parts are moved toward each other, a collision of the parts should be avoided as much as possible. For this purpose, when pushed together the housing parts are designed so as to engage with each other or so as to overlap each other. With the overlapping design the surfaces of the housing parts move closely past each other upon movement toward each other. With housing parts designed to engage with each other one housing part, for example, forms a receptacle into which the other housing part enters.

In an advantageous embodiment the housing parts may be at least partially flexible. Flexible housing parts can be used to further improve the adjustment to the received head. For this purpose, the flexible regions may be pressed against a head by a pressing arrangement, in particular pneumatically, by an air cushion or by a spring. If a head is thus introduced into the local coil arrangement, the flexible region or the completely flexible housing part can be pressed close to this specific head by the pressing arrangement. This leads to a further improvement in the adjustment, and therefore to an improved signal-to-noise ratio. As an alternative to a pressing arrangement the flexible regions may be made of viscofoam, in other words a viscoelastic foam. Viscofoam has a tendency to assume a certain form again in each case. This may be used to achieve automatic pressing as it were and therefore adjustment to the corresponding test object.

At least some of the housing parts can be equipped with fixing components, in particular fixing cushions and/or gripping jaws, for fixing a head in the head coil arrangement. In an embodiment of this type the head coils that can be adapted to various head sizes are advantageously also used for fixing the head, for which purpose a separate fixing element was previously required. For example, in one embodiment in which the housing has right and left housing parts that are linearly displaceable toward each other in the transverse direction of the head, fixing cushions can be provided in the region in which the ears are situated when the head is received. The ability of the housing parts to move toward each other then fixes the head through the fixing components in addition to providing adjustment to the size of the head.

It is likewise possible for the housing part(s) covering the ears of a head to embody noise-protection and/or communication components. In particular these noise-protection and/or communication components can form a unit with the above-mentioned fixing components. A further, basically separately provided component, namely headphones for noise-protection and/or communication, is advantageously also integrated into the head coil arrangement in this embodiment. This is made possible only by the ability of the housing parts to move toward each other since it is only then that the noise-protection and/or communication components can be brought sufficiently close to the ear of a received patient's head.

For better accessibility to the inside of the head coil arrangement at least one housing part may be removable from the arrangement. For example, one upper housing part or two upper housing parts may be removable, to allow a patient to introduce his or her head into the head coil arrangement with the requisite level of comfort.

A number of variants are conceivable for producing the ability of the housing parts to move toward each other or for operation. Since the head coil arrangement is to be inserted in a magnetic resonance unit, components not requiring electricity and materials that are not magnetically disruptive should be given preference.

It is possible for the mobility to be achieved purely mechanically and for the components allowing mobility to be activated manually. One advantage of manual operation is that the operator can immediately assess whether the head coil arrangement possibly encloses the patient's head too tightly and then, for example, presses or causes an unpleasant sensation.

Thus in the case of housing parts guided in linear guides, the housing parts can be moved via an actuator designed as a slide.

Alternatively, the housing parts can be moved by a gear or a screw mechanism. An easily reachable hand wheel that is provided on the side of the head coil arrangement is then expedient as an actuator for the movable housing parts.

In a further alternative embodiment, a pneumatic arrangement may be provided as a drive for moving the housing parts. A piston for example, which drives the housing parts guided in linear guides, may be used in this case. A pneumatic drive of this type could also be provided from a distance.

Alternatively a motor may be provided as a drive for moving the housing parts. So that there is no disruption to the imaging signals it is expedient in this embodiment to arrange the motor so as to be remote from the actual local coil arrangement. The driving force of the motor can be transmitted, for example, by belts or the like.

In particular when using a motor, but also when using a pneumatic drive, it can be expedient to provide a sensor with which the pressure of the housing parts on a head or the spacing of the housing parts from a head can be measured, and the motor or the pneumatic arrangement can be controlled with the signal of the sensor. This prevents the housing from enclosing the patient's head too tightly. Infrared or ultrasonic proximity sensors, for example, are suitable as sensors. Piezo pressure sensors may also be used.

In particular when constructing a head coil arrangement of this type, care should be taken to maintain the connections within the individual coils as well as the decoupling conditions. It is therefore expedient for parts of a coil arranged on or in different housing parts to be electrically conductively connected by preferably flexible connections. In the simplest case this may be en electrical wire connection that connects separately arranged parts of an individual coil. Sliding contacts are also possible as connections. Since the displacement of the housing parts toward each other is usually in a range of about 1.5 to 2 cm, straight pieces may be used in the overlapping region of the housing parts when using sliding contacts, for example.

Care should also be taken that the overlapping area of the individual coils is substantially constant. This overlapping area is used for decoupling the individual coils.

To secure the coils to the housing parts, the coils are first of all constructed on a flexible printed circuit board material. The arrangement of coils on printed circuit board material is conventionally about 0.1 to 0.2 mm thick. The printed circuit boards with the coils thereon can be provided on the housing parts in various ways, for example by way of a plug-in connector. Alternatively, the coils can be formed directly in or on the housing part.

In particular thirty-two or more individual coil elements, and consequently thirty-two or more receiving channels, may be produced in the head coil arrangement according to the invention.

DESCRIPTION OF THE PREFERRED EMBODIMENTS

Figure 1:
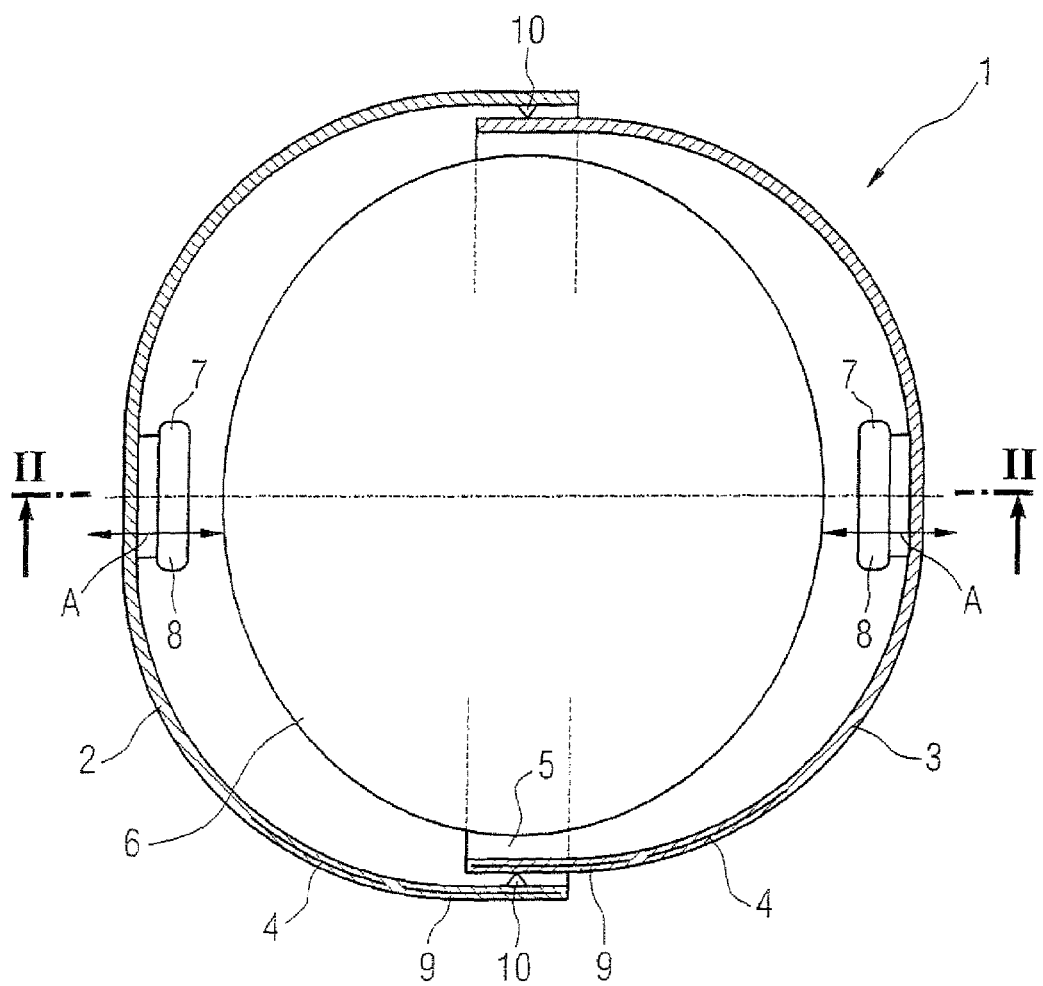
FIG. 1 shows a vertical section through a head coil arrangement according to a first embodiment of the invention.

FIG. 1 shows a vertical section through a head coil arrangement 1 according to a first embodiment. The arrangement 1 has a housing formed by a left housing part 2 and a right housing part 3. The housing parts 2 and 3 are guided in a linear guide (not shown in detail) and can therefore be linearly moved toward each other in the transverse direction of the head, as is indicated by arrow A. Displacement of the housing parts 2 and 3 toward each other is possible by way of manual actuators (not shown in detail), for example a slide or a hand wheel coupled via a gear or screw mechanism. Individual coils 4 that are integrated in the housing parts 2 and 3 are provided which are only partially indicated in FIG. 1.

The right housing part 3 is designed so it may be introduced into the left housing part 2, whereby an overlapping region 5 is produced. The internal volume of the local coil arrangement 1 becomes smaller by the amount of this overlapping region 5. It is consequently possible to adjust the local coil arrangement to the size of a head 6, illustrated only in outlines in FIG. 1.

The left and right housing parts 2 and 3 also have components 7 arranged in the region of the ears of the head 6 and which serve several purposes. Fixing cushions 8 are used to fix the head since the head has to be immobile during magnetic resonance imaging that may take a long time. The fixing cushions 8 are also used as pads for headphones, so a noise-protection function and a communication function are achieved. The components 7 therefore act as both fixing components and as noise-protection and communication components.

In some arrangements of the individual coils 4 it may be necessary for parts 9 of a single coil element 4 of this type to be arranged on different housing parts 2, 3. In this case a conductive connection must be ensured between the parts 9. In the present example the surfaces of the housing parts 2 and 3 run parallel in the overlapping region. Sliding contacts 10 are therefore provided on the left housing part 2 and these connect the coil parts 9. A flexible wire connection for example would alternatively be conceivable as a connection element.

Figure 2:
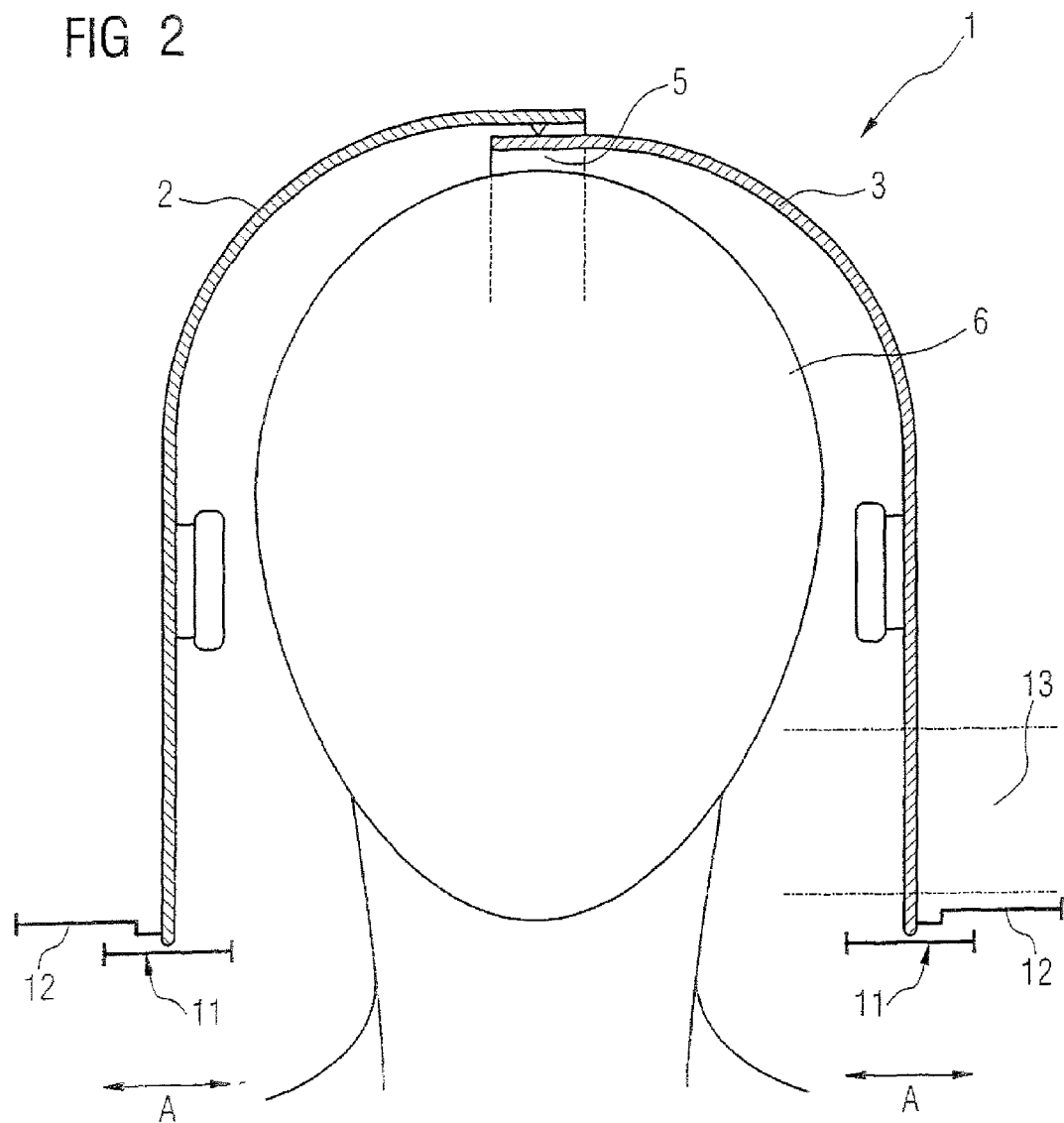
FIG. 2 shows a horizontal section through the head coil arrangement of FIG. 1 along the line II-II of the invention.

FIG. 2 shows a horizontal section of the coil arrangement 1 along the line II-II of FIG. 1. It may be seen therein that the left and right housing parts 2 and 3 also overlap the head 6 in order to form the overlapping region 5. The housing parts 2 and 3 are guided in linear guides 11, which are shown only in outlines, wherein they may be moved along the arrow A by a slide 12 that is also only shown in outlines. The mobility extends in this connection for example to the centimeter range, so decoupling of the individual coils 4 is not affected as a result of the relatively small displacement.

In the illustrated exemplary embodiment it can be seen that in the region 13 of the patient's neck the housing parts 2 and 3 are not adjusted to the neck. An adjustment of the shape of the housing parts 2, 3 would also be conceivable here, however, to achieve the greatest possible proximity to the head 6 even when acquiring images of the cerebellum, for example.

Figure 3:
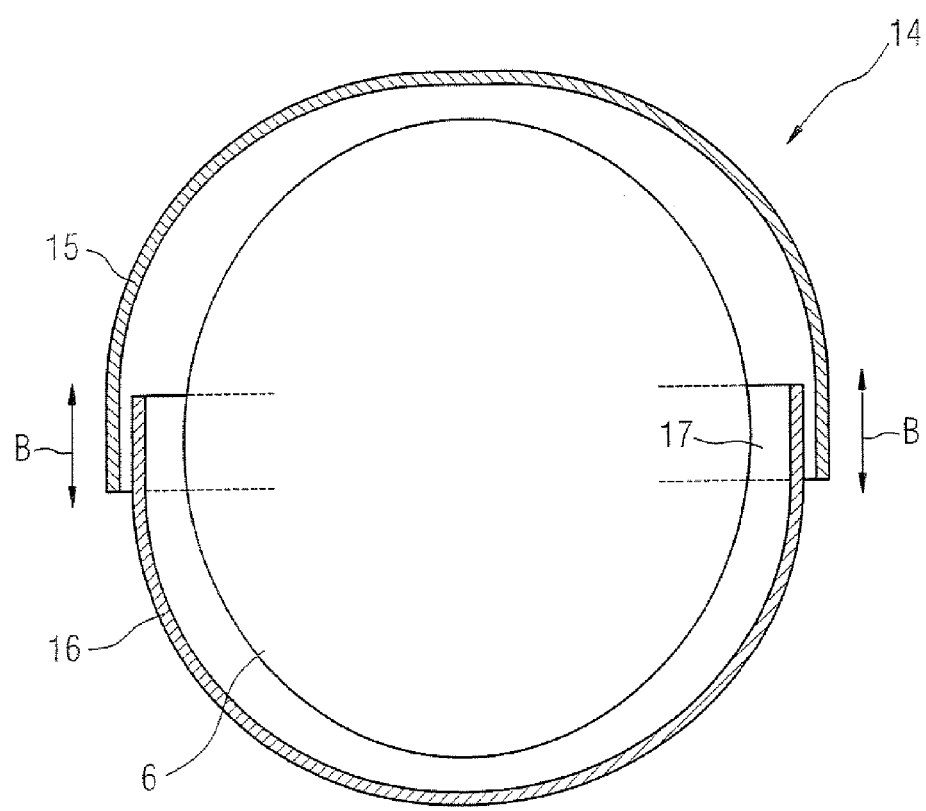
FIG. 3 shows a vertical section through a head coil arrangement according to a second embodiment of the invention.

FIG. 3 shows a vertical section through a head coil arrangement 14 according to a second embodiment. In this case the housing is divided into an upper housing part 15 and a lower housing part 16. The housing parts 15, 16, as indicated by arrow B, can be moved toward each other in the lengthwise direction of the head. For this purpose the housing parts 15, 16 are guided by means of linear guides (not shown in detail) here as well. Again, upon movement of the housing parts 15, 16 toward each other an overlapping region 17 is produced by which the internal volume of the head coil arrangement 14 is reduced, so adjustment to a head 6 (that is shown only schematically) is made possible.

Figure 4:
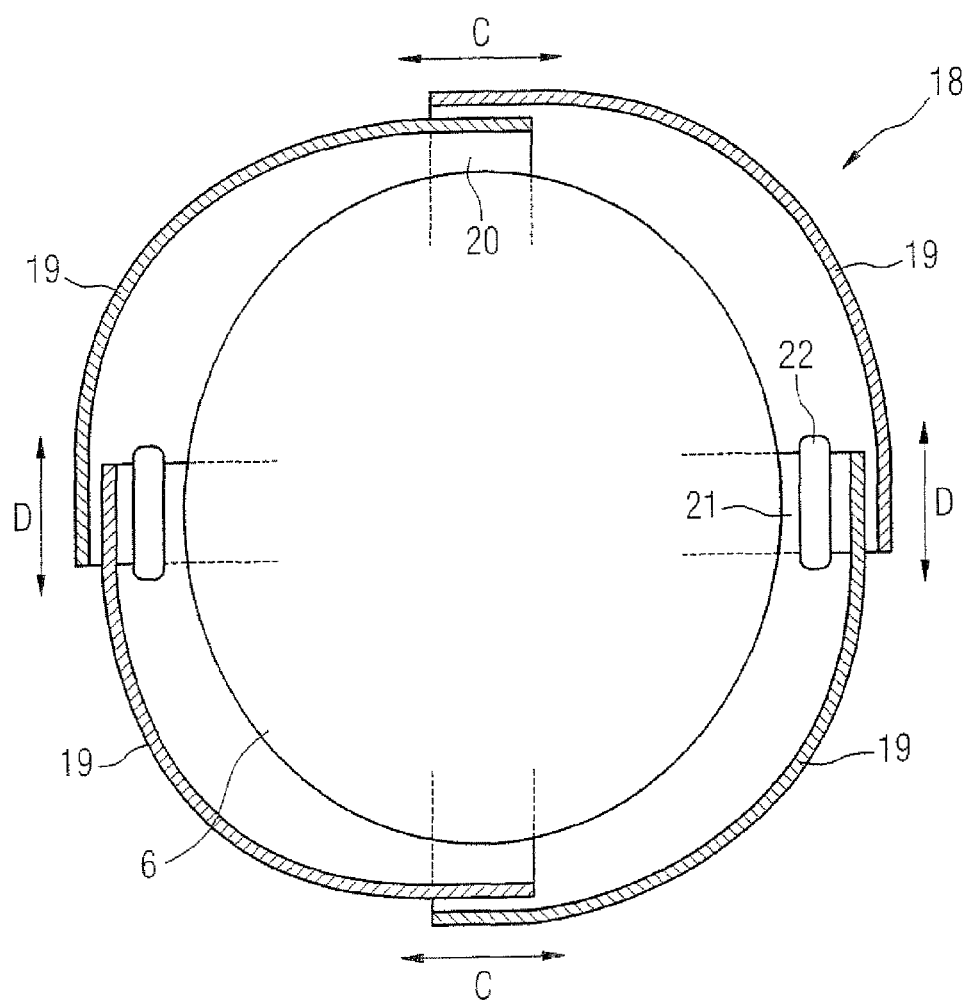
FIG. 4 shows a vertical section through a head coil arrangement according to a third embodiment of the invention.

FIG. 4 shows a vertical section through a head coil arrangement 18 according to a third exemplary embodiment. Here four housing parts 19 that each substantially cover a quarter of the head 6 are provided and these may each be moved in the transverse direction of the head 6, as indicated by arrow C, and in the lengthwise direction of the head 6, as indicated by arrow D, thus in two directions that are mutually perpendicular. Overlapping regions 20, 21 are therefore produced in both directions, so very flexible adjustment of the head coil arrangement 18 to different sizes of head 6 is possible. Components 22 are again provided on two of the housing parts 19 in the region of the ears of the head 6 and, as in the first exemplary embodiment, fulfill fixing, noise-protection and communication functions.

The housing parts 19 are guided by two linear guides (not shown in detail) respectively which, for example may be manually operated from the outside by a slide or hand wheel.

Figure 5:
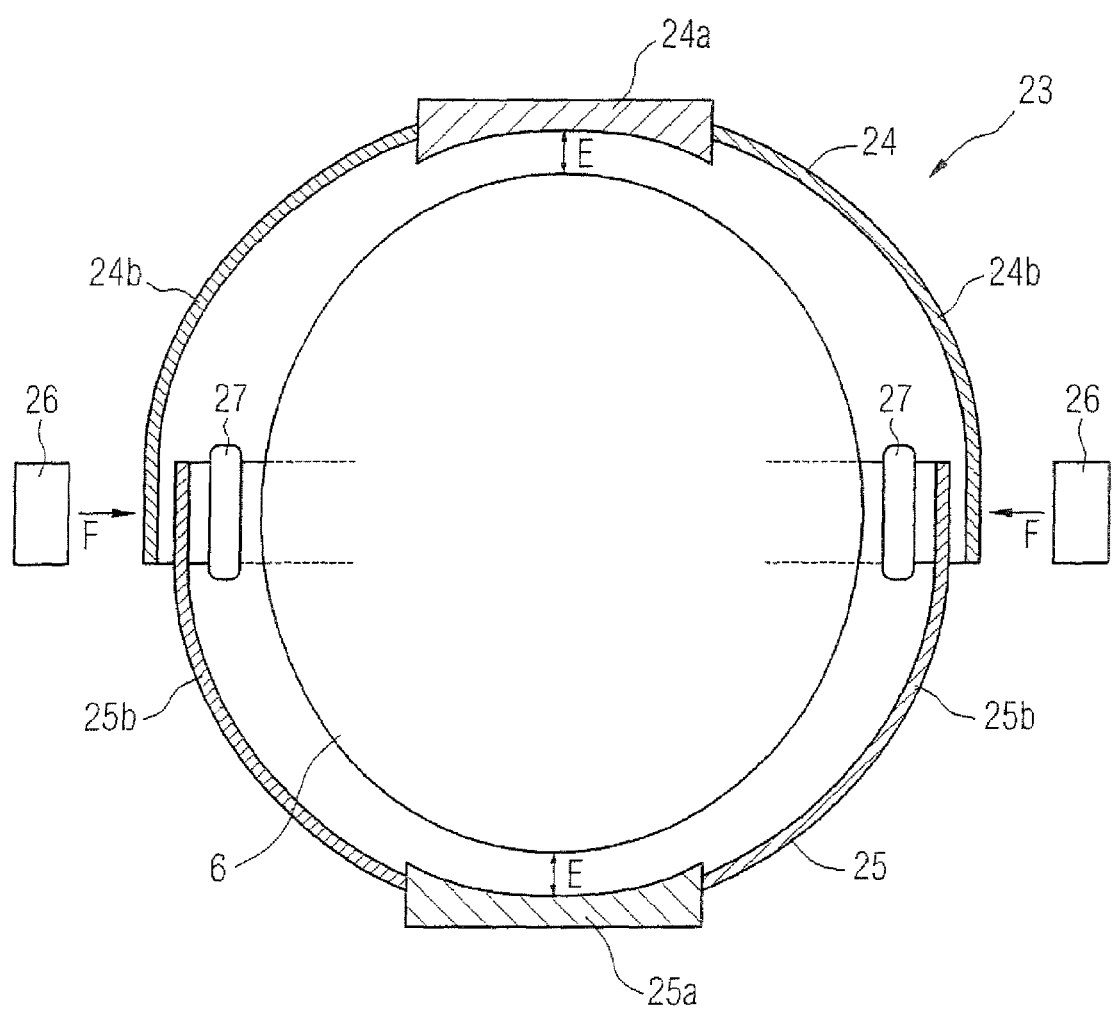
FIG. 5 shows a vertical section through a head coil arrangement according to a fourth embodiment of the invention.

FIG. 5 shows a vertical section through a fourth embodiment of a head coil arrangement 23. An upper housing part 24 and a lower housing part 25 are again provided here, it being possible for the housing parts 24, 25 to move toward each other in the lengthwise direction of the head 6, as symbolized by the arrow E. In this embodiment the housing parts 24 and 25 have substantially rigid housing part regions 24a, 25a and flexible housing part regions 24b and 25b. The flexible regions 24b and 25b are produced for example from a flexible plastics material. It is also possible to use a viscofoam that allows the flexible regions 24b and 25b to automatically adjust to the shape of the head 6. In this example however press-on elements 26 of which only the basic structure is shown are provided, which may be designed, for example, pneumatically, as air cushions or a spring. The press-on elements 26 press the flexible housing regions 24b and 25b along the arrow F onto the head 6, it being possible to achieve a relatively large-area press-on effect by way of an air cushion. The press-on effect allows the flexible regions 24b and 25b to be able to adjust the shape of the head 6 in an optimally ideal manner.

Cushion-like or padding-like components 27 are also provided here that can fulfill fixing, noise-protection and communication functions. The press-on effect of the press-on element 26 also consequently fixes the head by means of components 27. The components 27 come into contact with the ears of the head 6, so the noise-protection and communication functions are fulfilled.

Figure 6:
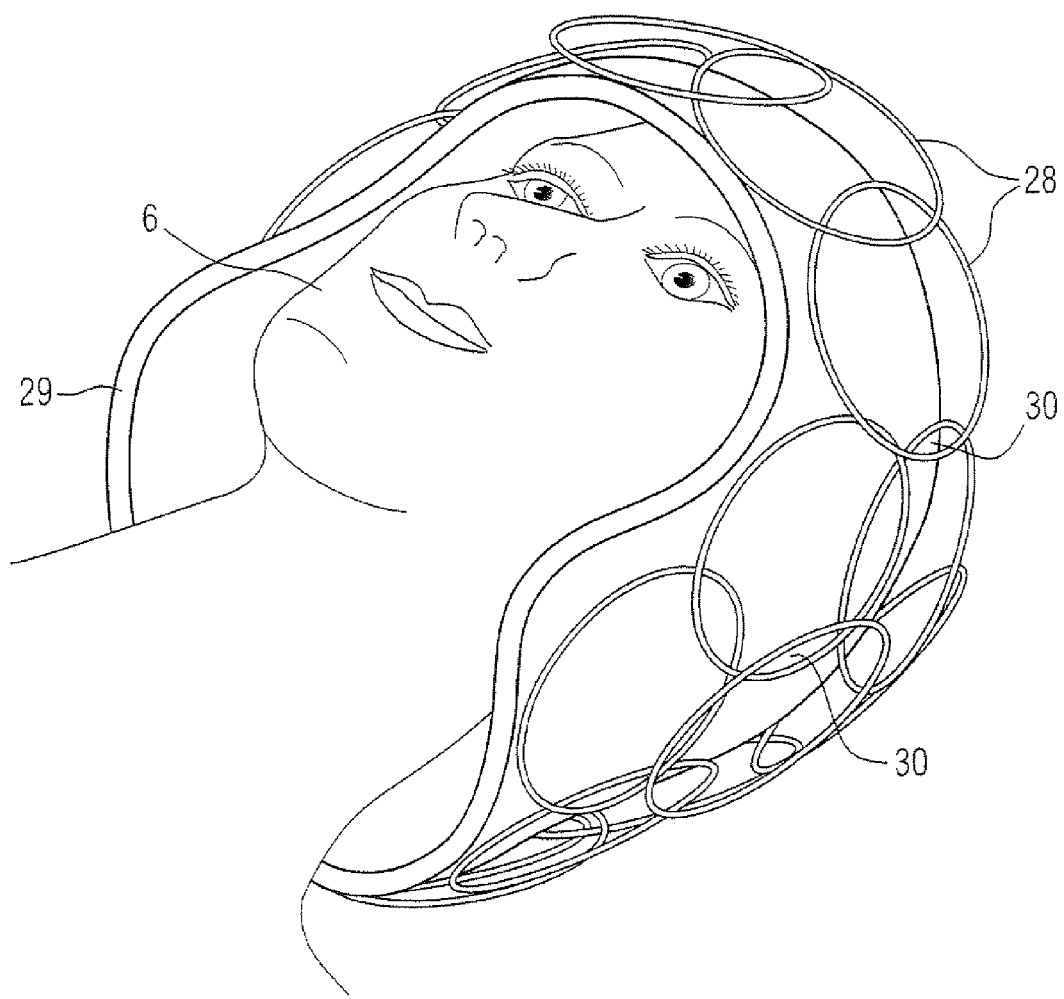
FIG. 6 shows an arrangement of coils on the housing of a head coil arrangement in accordance with the invention.

FIG. 6 shows in the form of a basic outline an arrangement of coils 28 on a housing 29 of a head coil arrangement. The coils 28 each have overlapping regions 30 that produce decoupling of the individual coils 28. Other arrangements of coils 28 are also conceivable.

Although some features are mentioned herein only in the context of a specific embodiment, the transfer of certain features between embodiments is possible. Thus for example in the embodiments according to FIGS. 1 to 4, housing regions or entire housing parts can be of flexible construction. A suitable press-on element may then also be provided at these locations. The capacity of the housing parts to move toward each other can be achieved in different ways in all exemplary embodiments as can the corresponding actuator. Thus a linear guide, a gear or a transformation of a gear to a linear guide are conceivable. A slide or a hand wheel for example are conceivable as the actuator.

With the illustrated exemplary embodiments it is also possible to allow a drive for the movable housing parts using a motor. Even a pneumatic drive may be considered. With drives that are remotely controlled, however, care should be taken that there is not excessive contact of the housing parts with the head. Sensors for example, which measure the spacing of the housing parts from the head or the pressure of the housing parts on the head, may be provided for this purpose. The motor or the pneumatic arrangements are then controlled as a function of the signals from the sensor means, which for example may be designed as infrared or ultrasonic proximity sensors, such that an unpleasant effect or injury to the patient is avoided.

Although modifications and changes may be suggested by those skilled in the art, it is the intention of the inventor to embody within the patent warranted hereon all changes and modifications as reasonably and properly come within the scope of his contribution to the art.

I claim as my invention:

1. A head coil arrangement for a magnetic resonance device, comprising:
   a plurality of radio-frequency coils;
   a housing on which or in which said plurality of radio-frequency coils is carried;
   said housing comprising at least two housing parts that define a circumference of the housing, said housing parts comprising a mechanical interaction with each other configured to permit said housing parts to move toward each other to adjust said housing to different head sizes by changing a size of said circumference, said housing parts comprising linear guides that linearly guide said housing parts toward each other, in the linear guides; and a movement mechanism connected to at least one of said housing parts that is operable to move said housing parts toward each other, and a sensor that senses a pressure applied by said housing parts to a head received in said housing, said movement mechanism being controlled dependent on an output of said sensor.

2. A head coil arrangement as claimed in claim 1 wherein said housing parts mechanically interact with each other to linearly move toward each other.

3. A head coil arrangement as claimed in claim 2 wherein said housing parts mechanically interact with each other to move toward each other in at least one of a longitudinal direction and a transverse direction of a head to be received in the housing.

4. A head coil arrangement as claimed in claim 1 comprising four housing parts each covering substantially one quarter of a head received in the housing, each of said four housing parts being linearly moveable into perpendicular directions with respect to another of said four housing parts adjacent thereto.

5. A head coil arrangement as claimed in claim 4 wherein each housing part comprises two linear guides at opposite ends thereof.

6. A head coil arrangement as claimed in claim 1 wherein said housing parts mechanically interact with each other so that as the housing parts are moved toward each other, said housing parts engage or overlap each other.

7. A head coil arrangement as claimed in claim 1 wherein said housing parts are at least partially flexible.

8. A head coil arrangement as claimed in claim 7 wherein each of said housing parts comprises a flexible region configured to press against a head received in said housing, with a pressing element located in the flexible region.

9. A head coil arrangement as claimed in claim 8 wherein said pressing element is a pressing element selected from the group consisting of pneumatic elements, air cushions, and springs.

10. A head coil arrangement as claimed in claim 7 wherein said flexible region is comprised of viscofoam.

11. A head coil arrangement as claimed in claim 1 wherein at least one of said housing parts comprises a fixing element to fix a head in the housing.

12. A head coil arrangement as claimed in claim 11 wherein said fixing element is an element selected from the group consisting of fixing cushions and gripping jaws.

13. A head coil arrangement as claimed in claim 1 wherein said housing parts are configured to cover the ears of a head received in the housing and, in a region of each housing part covering an ear, comprise a component selected from the group consisting of noise-protection components and communication components.

14. A head coil arrangement as claimed in claim 1 wherein at least one of said housing parts is removable from said housing.

15. A head coil arrangement as claimed in claim 1 wherein said movement mechanism is a remotely-operable motor.

16. A head coil arrangement as claimed in claim 1 wherein said movement mechanism is a mechanism selected from the group consisting of a motor and a pneumatic mechanism.

17. A head coil arrangement as claimed in claim 1 wherein different coils in said plurality of coils are respectively mounted on different ones of said housing parts, and comprising a flexible connector that electrically conductively connects said different coils.

18. A head coil arrangement for a magnetic resonance device, comprising:

a plurality of radio-frequency coils;

a housing on which or in which said plurality of radio frequency coils is carried;

said housing comprising at least two housing parts that define a circumference of the housing, said housing parts comprising a mechanical interaction with an overlap of said two housing parts, configured to permit said two housing parts to move toward each other to change a size of said overlap to adjust said housing to different head sizes by changing a size of said circumference of said housing, said housing parts comprising linear guides that linearly guide said housing parts toward each other, in the linear guides; and a movement mechanism connected to at least one of said housing parts that is operable to move said housing parts toward each other, and a sensor that senses a pressure applied by said housing parts to a head received in said housing, said movement mechanism being controlled dependent on an output of said sensor.

19. A head coil arrangement for a magnetic resonance device, comprising:

a plurality of radio-frequency coils;

a housing on which or in which said plurality of radio frequency coils is carried, said housing being configured to surround a circumference of a patient's head in a plane of the head; and said housing comprising a plurality of housing parts that define a circumference of the housing, said housing parts comprising a mechanical interaction that mechanically interact with each other configured to permit said housing part to move toward each other to adjust said housing in a first direction in said plane and in a second direction in said plane that is parallel to said first direction, in order to adjust said housing to different head sizes by changing a size of said circumference of said housing, said housing parts comprising linear guides that linearly guide said housing parts toward each other, in the linear guides; and a movement mechanism connected to at least one of said housing parts that is operable to move said housing parts toward each other, and a sensor that senses a pressure applied by said housing parts to a head received in said housing, said movement mechanism being controlled dependent on an output of said sensor.

20. A head coil arrangement as claimed in claim 19 wherein said housing is configured to circumferentially surround the patient's head in a transverse plane.

\* \* \* \* \*